(12) United States Patent
Knutsson

(10) Patent No.: US 9,522,255 B2
(45) Date of Patent: Dec. 20, 2016

(54) POLYMERIC CATHETER NEEDLE TIP SHIELDING DEVICE

(75) Inventor: Per Knutsson, Helsingborg (SE)

(73) Assignee: Vigmed AB, Helsingborg (SE)

( * ) Notice: Subject to any disclaimer, the term of this patent is extended or adjusted under 35 U.S.C. 154(b) by 0 days.

(21) Appl. No.: 13/640,703

(22) PCT Filed: Apr. 12, 2011

(86) PCT No.: PCT/SE2011/050443
§ 371 (c)(1),
(2), (4) Date: Oct. 11, 2012

(87) PCT Pub. No.: WO2011/129753
PCT Pub. Date: Oct. 20, 2011

(65) Prior Publication Data
US 2013/0030371 A1    Jan. 31, 2013

(30) Foreign Application Priority Data
Apr. 13, 2010 (SE) ...................................... 1050360

(51) Int. Cl.
*A61M 25/06* (2006.01)
*A61M 5/32* (2006.01)

(52) U.S. Cl.
CPC ........ *A61M 25/0618* (2013.01); *A61M 5/3273* (2013.01); *A61M 25/0606* (2013.01)

(58) Field of Classification Search
CPC ............................................... A61M 25/0618
(Continued)

(56) References Cited

U.S. PATENT DOCUMENTS 3,469,579 A * 9/1969 Hubert ......................... 604/533
3,589,361 A * 6/1971 Loper et al. ............. 604/165.03
(Continued)

FOREIGN PATENT DOCUMENTS

CN       1547493 A    11/2004
CN    101500637 A    8/2009
(Continued)

OTHER PUBLICATIONS

International Search Report for PCT/SE2011/050443 Mailed Nov. 7, 2011.
(Continued)

*Primary Examiner* — Theodore Stigell
*Assistant Examiner* — Benjamin Koo
(74) *Attorney, Agent, or Firm* — Fishman Stewart PLLC

(57) ABSTRACT

The present invention discloses a catheter instrument (1000) comprising a needle tip shielding device (100), a needle (303), a needle carrying unit, and a catheter unit, said catheter unit comprising a catheter hub (200) and a catheter (201), and said needle tip shielding device (100) and said catheter hub (200) being separable from one another, wherein said needle tip shielding device (100) is kept in contact with said catheter unit upon withdrawal of said needle (303) via at least one interface surface between said needle tip shielding device (100) and said catheter unit, and wherein said at least one interface surface of said needle tip shielding device (100) being at least partly of a first polymeric material and said at least one interface surface of said catheter unit being at least partly of a second polymeric material.

12 Claims, 10 Drawing Sheets

(58) Field of Classification Search
USPC .................................................. 604/164.08
See application file for complete search history.

(56) References Cited

U.S. PATENT DOCUMENTS

| | | | |
|---|---|---|---|
| 4,820,277 A | 4/1989 | Norelli | |
| 4,929,241 A | 5/1990 | Kulli | |
| 4,982,842 A | 1/1991 | Hollister | |
| 5,053,017 A | 10/1991 | Chamuel | |
| 5,132,369 A | 7/1992 | Yasuda et al. | |
| 5,135,504 A | 8/1992 | McLees | |
| 5,151,089 A | 9/1992 | Kirk et al. | |
| 5,186,611 A | 2/1993 | Orgain | |
| 5,242,417 A | 9/1993 | Paudler | |
| 5,312,369 A | 5/1994 | Arcusin | |
| 5,344,408 A | 9/1994 | Partika | |
| 5,458,658 A | 10/1995 | Sircom | |
| 5,490,841 A | 2/1996 | Landis | |
| 5,558,651 A | 9/1996 | Crawford et al. | |
| 5,599,313 A | 2/1997 | Gyure et al. | |
| 5,603,699 A | 2/1997 | Shine | |
| 6,197,001 B1 | 3/2001 | Wilson | |
| 6,413,243 B1 | 7/2002 | Geist | |
| 6,616,630 B1* | 9/2003 | Woehr et al. | 604/110 |
| 7,704,239 B2* | 4/2010 | Raulerson et al. | 604/258 |
| 7,935,080 B2* | 5/2011 | Howell et al. | 604/110 |
| 8,038,654 B2 | 10/2011 | Lim et al. | |
| 8,337,471 B2* | 12/2012 | Baid | 604/263 |
| 8,403,886 B2* | 3/2013 | Bialecki et al. | 604/110 |
| 8,414,539 B1* | 4/2013 | Kuracina et al. | 604/192 |
| 8,632,500 B2 | 1/2014 | Knutsson | |
| 2002/0099342 A1 | 7/2002 | Zurcher | |
| 2003/0105431 A1 | 6/2003 | Howell | |
| 2004/0049155 A1 | 3/2004 | Schramm | |
| 2004/0225260 A1 | 11/2004 | Villa et al. | |
| 2005/0277879 A1 | 12/2005 | Daga | |
| 2007/0038179 A1 | 2/2007 | Bialecki et al. | |
| 2007/0100296 A1 | 5/2007 | Hwang | |
| 2008/0097344 A1* | 4/2008 | McKinnon et al. | 604/263 |
| 2008/0208138 A1 | 8/2008 | Lim et al. | |
| 2008/0249478 A1 | 10/2008 | Ishikura | |
| 2009/0088696 A1 | 4/2009 | Harding et al. | |
| 2009/0163861 A1 | 6/2009 | Carlyon | |
| 2011/0160671 A1 | 6/2011 | Tanabe et al. | |
| 2012/0130321 A1 | 5/2012 | Woehr | |
| 2012/0136311 A1 | 5/2012 | Knutsson | |
| 2012/0296282 A1* | 11/2012 | Koehler et al. | 604/164.08 |
| 2013/0178800 A1 | 7/2013 | Domonkos et al. | |
| 2014/0121604 A1 | 5/2014 | Knutsson | |
| 2014/0135713 A1 | 5/2014 | Domonkos | |

FOREIGN PATENT DOCUMENTS

| | | |
|---|---|---|
| CN | 102470236 A | 8/2009 |
| CN | 202875975 | 4/2013 |
| EP | 0 657 184 A1 | 6/1995 |
| EP | 0 887 082 A2 | 12/1998 |
| EP | 2 016 963 A1 | 1/2009 |
| EP | 2 204 204 A1 | 7/2010 |
| GB | 2451153 | 1/2009 |
| JP | 2001-514943 A | 9/2001 |
| JP | 2001514943 A | 9/2001 |
| JP | 2002085558 A | 3/2002 |
| JP | 2005-529717 A | 10/2005 |
| JP | 2005529717 A | 10/2005 |
| JP | 2008-522739 A | 7/2008 |
| JP | 2008522739 A | 7/2008 |
| JP | 2010-500150 A | 1/2010 |
| SE | 1150633 A1 | 1/2013 |
| WO | WO-9908742 A1 | 2/1999 |
| WO | WO 01/68174 A2 | 9/2001 |
| WO | WO-2004000408 A1 | 12/2003 |
| WO | WO 2005/042080 | 5/2005 |
| WO | WO 2005/079891 A1 | 9/2005 |
| WO | WO-2006062983 A1 | 6/2006 |
| WO | WO 2006/079766 A1 | 8/2006 |
| WO | WO 2009/010847 | 1/2009 |
| WO | WO 2009/123025 A1 | 10/2009 |
| WO | WO-2009123025 A1 | 10/2009 |
| WO | WO 2011/019316 A1 | 2/2011 |
| WO | WO 2013/006134 A1 | 1/2013 |

OTHER PUBLICATIONS

Notification of Transmittal of International Preliminary Report on Patentability Mailed Jul. 17, 2012.
International Search Report dated Dec. 8, 2010 issued in International Application No. PCT/SE2011/050884.
International Search Report dated Jul. 11, 2011 issued in International Application No. PCT/SE2011/050443.
International Search Report dated Dec. 21, 2011 issued in International Application No. PCT/SE2011/051140.
International Search Report dated Sep. 27, 2012 issued in International Application No. PCT/SE2012/050771.
U.S. Appl. No. 14/076,374, filed Nov. 2013, Knutsson.
U.S. Appl. No. 14/130,868, filed Jan. 2014, Domonkos.
Chinese Office Action (with translation) dated Jul. 4, 2014 issued in Chinese Application No. 2011800189380.
Japanese Office Action (with translation) dated Dec. 16, 2014 issued in Japanese Application No. 2013-504851.

* cited by examiner

POLYMERIC CATHETER NEEDLE TIP SHIELDING DEVICE

This is a National Phase Application under 35 USC 371 of PCT/SE2011/050443, dated Apr. 12, 2011, and claims priority under 35 USC 365 (a)-(c) to Swedish Application No. 1050360-5, dated Apr. 13, 2010, the contents of which are incorporated herein by reference.

TECHNICAL FIELD

The present invention relates to a catheter instrument comprising a polymeric needle tip shielding device for the automatic safety shielding of a needle after its employment for introduction of a catheter tube.

BACKGROUND

The clinical utilization of a pointed hollow needle mounted inside a flexible catheter tube is well known in the medical art for the introduction of a catheter. In such a medical instrument, the catheter tube is positioned tightly around the needle in such a way as to allow the needle to slide and telescope along the length of the catheter tube. Before use, the tip of the needle is protruding slightly through the opening of the catheter tube to allow facile penetration through the skin. Upon puncturing of the skin and introduction of the needle, the distal end of the catheter tube is simultaneously brought into place inside the desired target body cavity of the patient, such as the inside of a blood vessel, for example a vein. The needle has then done its duty in assisting the introduction of the catheter and is withdrawn by being pulled backwards through the catheter. Upon release of the needle, the catheter is set in its intended working mode extending over a lengthier period of time and including, for example, periodical administration or infusion of fluids or medications in liquid form, the collection of blood samples and the like.

An unprotected released needle constitutes, however, a serious health hazard due to the fact that it may be contaminated with e.g. infectious agents originating from the patient's blood or other body fluids, in combination with the needle tip's inherent ability to easily penetrate skin. Hence, the medical personnel who are handling the released needle may acquire the corresponding disease, e.g. HIV or hepatitis, if by accident contacting it with their skin. In order to circumvent or alleviate the health hazards associated with such a released needle amongst other things, there has been much effort devoted to the development of various kinds of needle tip protectors with a special focus on automatic variants of a type which may be referred to as being "foolproof".

Factors of relevance for the design of automatic needle tip protectors include the choice of material and the protector's interaction with immediate contacting parts of the medical instrument.

With regard to the choice of material, protectors may be divided into two main categories, metallic or polymeric. Advantages of polymeric or plastic needle tip protectors, in comparison to metallic ones, include reduced noise or scraping vibrations as the needle is withdrawn from the catheter. In addition, they may be produced by e.g. molding, which offers greater design opportunities.

If the protector is mounted so that it is contacting a part of the medical device which may communicate with e.g. a vein of a patient, it is desirable to avoid the inclusion of sharp edges and the like in the design of the protector. Such edges or similar shapes may result in scrapings and release of particles or flakes which represents a health hazard to the patient. Thus, it is desirable to design the protector such that only smooth shapes of it is contacting critical parts of the medical device, such as the inside of a catheter hub.

Contacting smooth shapes of two bodies, such as the protector and a part of the medical instrument may, however, result in a significant attraction between these parts, especially if the contact area is large and they are pressed together. The underlying basis for this type of attraction include intermolecular attraction between the molecules of the two bodies, in which molecular van der Waals interactions and surface tension of the two bodies are important factors. Covalent bond formation between closely interacting surfaces may also contribute to the attraction. This type of attraction may become noticeable when the protector, or a part thereof, is about to be released from the contacting part of the medical device as a part of its intended function. The force needed to release the protector, or a part thereof, from the device then becomes significantly higher than expected. This effect, which will be referred to as "the attraction effect" from here on, may even adventure the intended function of the protector if relying on e.g. an automatic release of a part of the protector, such as a spring biased arm or the like, from a part of the medical device, such as the interior of the catheter hub.

GB2451153A by Poly Medicure Ltd discloses a needle safety device for an intravenous catheter apparatus that includes a base, which may be made of a plastic material, capable of receiving a needle between opposing jaws attached to the base and capable of being influenced by the needle. The jaws have a link connecting the jaws arranged a distance from the base. The jaws may move between an expanded position in which they interact with an obstruction within a wing housing of the intravenous catheter apparatus. The jaws permit relative movement of the needle with the base when expanded, close around a needle tip as it passes the jaws, and prevent relative movement of the needle with the base when the jaws are collapsed.

U.S. Pat. No. 5,135,504A by Donald J. McLees describes a needle tip guard that may be made of a plastic material. The presence of the needle keeps the end of the guard flared out and thereby retained inside the catheter hub by e.g. a retaining ring held tightly therein until the needle is withdrawn from the catheter. At that time a slightly widened portion of the needle tip catches the guard, forcing the end of the guard to close over the tip and pulling the guard from the hub.

The function of the needle tip guards described in GB2451153A and U.S. Pat. No. 5,135,504A relies on the presence of one or several obstructions, e.g. protuberances or grooves, of the inside of the catheter hub for keeping the guards at place there until the needle is withdrawn from the hub. Disadvantages of the need of such obstructions include the need to use specially designed catheter hubs which are more expensive and difficult to produce in comparison to simpler standard catheter hubs. In addition, nowhere in GB2451153A or U.S. Pat. No. 5,135,504A is the attraction effect, or a corresponding phenomenon, mentioned. It can therefore not be ruled out that one or several of the guards described therein has been designed without taking this effect into account and, hence, that the function and/or safety of the corresponding guard may be compromised due to this.

Hence, an improved device for automatic shielding of the needle tip of a needle after its employment for introduction of a catheter tube is desired.

SUMMARY

It is an object of the present invention, considering the disadvantages mentioned above, to provide a needle tip shielding device which may be used in a relatively simple standard catheter hub.

It is another object of the present invention to provide a catheter instrument which desired function is minimally affected by the attraction effect.

It is yet another object of the present invention to provide a needle tip shielding device which may be easily manufactured at a low cost.

It is yet another object of the present invention to provide a needle tip shielding device which is highly safe for the patient as well as the user.

It is yet another object of the present invention to provide a needle tip shielding device which does not result in scraping vibrations and/or sounds as the needle is withdrawn through the same.

These and other objects, which will appear from the following description, have now been achieved by a device according to one aspect of the present invention which comprises a catheter instrument, comprising a needle tip shielding device, a needle, a needle carrying unit, and a catheter unit, the catheter unit comprising a catheter hub and a catheter, and the needle tip shielding device and the catheter hub are separable from one another; wherein the needle is comprising a needle tip; the catheter hub comprises: a catheter hub distal end and a catheter hub proximal end, the catheter hub distal end having the catheter extending therefrom, and a catheter hub opening, the catheter hub opening defining a catheter hub annular space; the needle carrying unit further comprising: a needle carrying unit distal end and a needle carrying unit proximal end, the needle carrying unit distal end having the needle extending therefrom; when the needle is in the ready position, in which the needle projects into the catheter, the needle is partly disposed within the needle tip shielding device and slidingly engaged with the needle carrying unit; when the needle is in a fully retracted position, in which the needle tip is completely withdrawn from the catheter, the needle tip shielding device is distally shielding the needle tip and a stop member, preventing the needle tip shielding device from distal movement relative to the needle in the fully retracted position; characterized in that the needle tip shielding device is kept in contact with the catheter unit in the ready position via at least one interface surface between the needle tip shielding device and the catheter unit; the at least one interface surface of the needle tip shielding device being at least partly of a first polymeric material and the at least one interface surface of the catheter unit being at least partly of a second polymeric material.

According to another aspect of the present invention, the first polymeric material is a polymer being different from the second polymeric material, and the second polymeric material comprising at least one polymer produced from substituted or unsubstituted ethene by a polymerization reaction in which the double bond of said ethane is converted to a single bond.

According to yet another aspect of the present invention, the needle tip shielding device is positioned in the catheter hub annular space in the ready position.

According to yet another aspect of the present invention, the needle tip shielding device comprises a resilient biasing portion having a first position and a second position, the first position being characterized by the resilient biasing portion abutting the needle shaft of the hollow needle in the ready position, and the second position being characterized by the resilient biasing portion shielding the needle tip in the fully retracted position.

According to yet another aspect of the present invention, the resilient biasing portion comprises at least one resilient arm.

According to yet another aspect of the present invention, the needle carrying unit comprises a hole.

According to yet another aspect of the present invention, the at least one interface surface comprises at least one protuberance or friction element for detachably engaging the needle tip shielding device and the catheter hub.

According to yet another aspect of the present invention, the stopping member comprises an expansion region on the needle near the needle tip for engagement with the needle tip shielding device or the needle carrying unit, thereby preventing distal movement of the needle tip shielding device relative to the needle.

According to yet another aspect of the present invention, the stopping member comprises at least one friction element, or a foldable string or stripe connected at its distal end to the needle tip shielding device and connected at its proximal end to a needle unit, the length of the foldable string or stripe being less than the length of the needle.

According to yet another aspect of the present invention, there is disclosed a polymeric needle tip shielding device for assembly in the catheter instrument, comprising a hole and a resilient arm extending from an attachment point; wherein the resilient arm has a resting state from which it may be forced to yield free passage through the hole in an axial direction, the resilient arm together with a back-hooking elongation thereof having an L-shaped form for protecting a needle tip of a hollow needle extending through the hole; any straight imaginary line extending longitudinally through the hole in the axial direction coincides with a point on the surface of the resilient arm in between the attachment point and an inner corner in the L-shaped form of the resilient arm, when the resilient arm is in the resting state; the any straight imaginary line coincides with a point on the surface of the back-hooking elongation, or with a point on the surface in between the attachment point and the corner, when the resilient arm is protecting the needle tip from accidental contact in cooperation with the back-hooking elongation; and the resilient arm or the back-hooking elongation has a maximum of one external point of contact, the point of contact being a contact with any part of the hollow needle, when used.

According to yet another aspect of the present invention, the needle tip shielding device is provided with at least one protuberance or at least one slit, or with a friction element in the form of a rough outer surface.

According to yet another aspect of the present invention, the needle tip shielding device is made of a thermoplastic polymer comprising covalently bond 0 or S atoms.

Further features of the invention and its embodiments are set forth in the appended claims.

BRIEF DESCRIPTION OF THE DRAWINGS

These and other aspects, features and advantages of which the invention is capable will be apparent and elucidated from the following description of non-limiting embodiments of the present invention, reference being made to the accompanying drawings, in which.

DETAILED DESCRIPTION OF THE EMBODIMENTS

Figure 1:
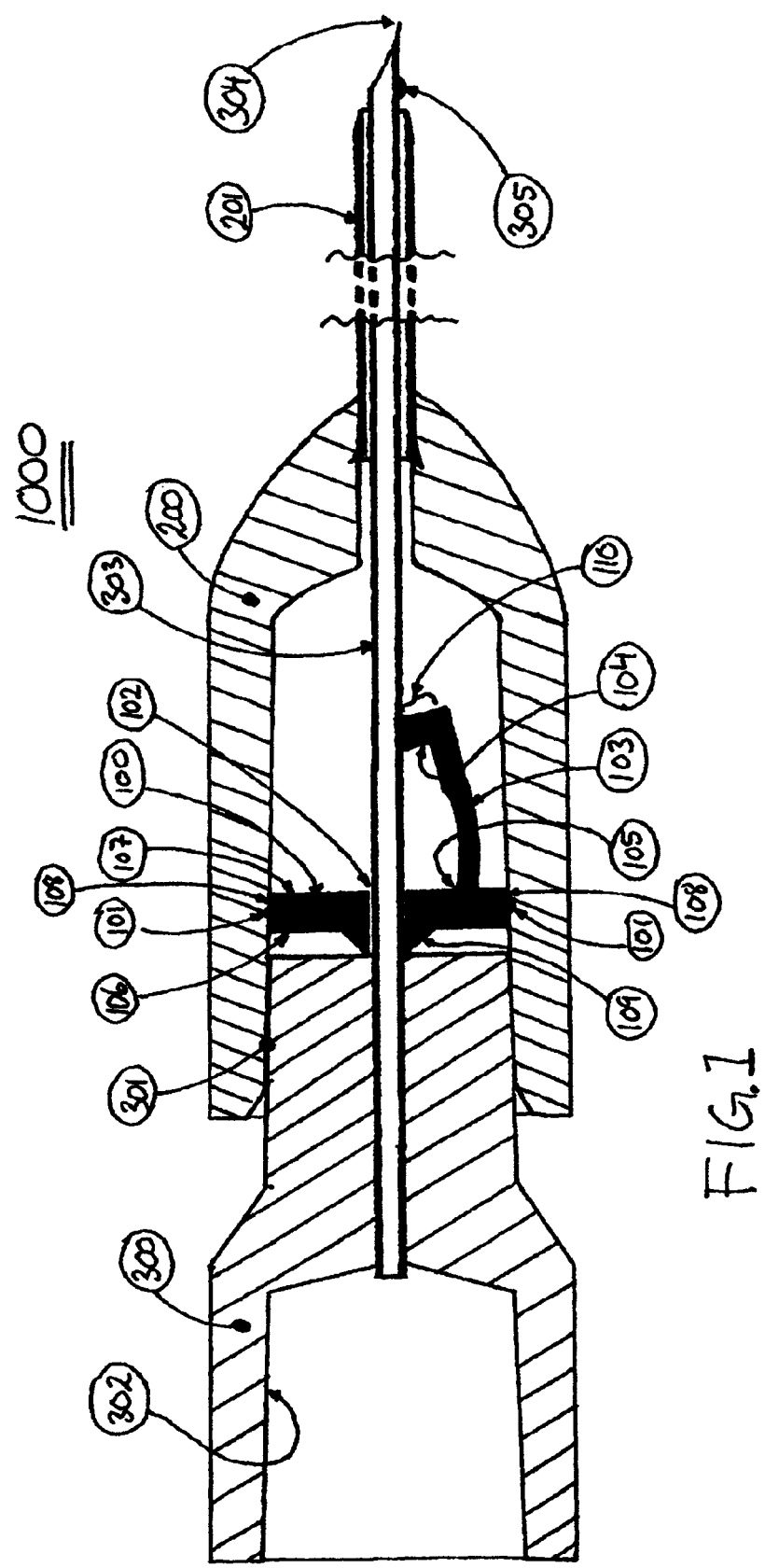
FIG. 1 is a cross section view from the side of a catheter instrument 1000 in the ready mode, i.e. before its use for the introduction of a catheter tube, comprising a needle tip shielding device 100 according to an embodiment of the present invention, a catheter hub 200 and a needle unit 300.

Embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

Embodiments of the present invention will now be described below with reference to FIGS. 1 to 9.

The Catheter Instrument 1000

The catheter instrument 1000 according to the present invention, comprise essentially a needle tip shielding device 100, a needle 303, a needle carrying unit, and a catheter unit.

The needle 303 is preferably a hollow needle 303, but may also be other types of needles, e.g. a solid needle or the like.

The needle tip shielding device 100 comprise means for protecting the needle tip 304 of the hollow needle 303 when it is withdrawn from the catheter unit, i.e. in the fully retracted position, whereby the protecting function of the needle tip shielding device 100 is activated. These means may, however, allow the hollow needle 303 to slide back and forth inside the catheter unit when the protecting function is not activated, such as in the ready position (the ready mode), to essentially allow a user to withdraw the hollow needle 303 after insertion of a catheter 201 of the catheter instrument 1000. Preferably, these means comprise a resilient biasing portion which in a first position, which corresponds to e.g. the ready position of the catheter instrument 1000, abut the shaft of the hollow needle 303. In a second position, which corresponds to the fully retracted position of the hollow needle 303, this resilient biasing portion prevents the hollow needle 303 to be pushed forward relative the needle tip shielding device 100 and simultaneously shields the needle tip 303 from accidental contact. Additional suitable non-resilient means include, for example, arms or the like which are forced into the second position by springs, o-rings or the like, as known in the art.

The catheter instrument 1000 may preferably comprise a needle carrying unit for helping directing the longitudinal movement of the hollow needle 303 as it is withdrawn or pushed forward relative the catheter unit. The needle carrying unit is preferably integrated with the needle tip shielding device 100. It may also consist of a separate part or of a part integrated with other parts of the catheter instrument 1000. Preferably the needle carrying unit is constituted by one or several holes, such as a hole 102, with a diameter slightly larger than the shaft of the hollow needle 303. Additional needle carrying units include springs, clips or the like which abut the needle shaft of the hollow needle from opposite sides. The connection of the needle carrying unit to the catheter unit, preferably in or at the proximal end of the catheter unit, will thus restrict movement of the hollow needle 303 in a direction perpendicular to the longitudinal direction of the catheter unit.

The catheter unit comprises a catheter hub 200, from which distal end a catheter 201 is extending. The internal volume of the catheter hub 200, i.e. the catheter hub annular space, is limited by the internal surface of the catheter hub 200, the distal end, and the plane of the proximal opening. Preferably, the needle tip shielding device 100 is detachably attached inside the catheter hub 200 in the ready position, in the catheter hub annular space, to allow for connection of a needle unit 300 at the proximal end of the catheter hub, preferably in the catheter hub annular space. Advantageously, no additional extra parts are thus needed for the employment to join the needle unit 300, the catheter unit, and the needle tip shielding device 100. The needle tip shielding device 100 of the present invention may, however, be linked to the catheter hub 200 outside the catheter hub annular space by such additional parts known in the art.

Means for detachably attaching the needle tip shielding device 100 inside the catheter hub 200 include, for example, at least one protuberance 101 located on a surface, such as an outer surface 108, which is in contact with the inner surface of the catheter hub 200. Such protuberance 101 may make an imprint in the inner surface of the catheter hub 200. Alternatively the inner surface of the catheter hub 200 may be provided with at least one protuberance which makes an imprint in the contacting surface of the needle tip shielding device 100. Other means include attachment by friction. The inner surface of the catheter hub 200 and/or the contacting surface of the needle tip shielding device 100 are then provided with a suitable roughness, as known in the art, for control of the force needed to detach the needle tip shielding device 100 from the catheter hub 200. Thus, one or both of these surfaces are provided with a friction element in the form of roughness. For example, the outer surface 108 of the needle tip shielding device 100 may be provided with a friction element in the form of a rough surface with a roughness of, for example, at least 0.4 Ra, preferably 2.2 to 3.3 Ra. Yet more means include one or several protuberances or grooves located on the needle tip shielding device 100, such as on a comprising resilient biasing part thereof, which engage with corresponding groves or protuberances, respectively, located in the catheter hub 200, as known in the art. Upon withdrawal of the hollow needle 303, this engagement ceases due to relaxation of a part which is forced out of its resting position by the needle shaft, and the needle tip shielding device 100 is released. The needle tip shielding device 100 may also be provided with slits 111 suitably shaped as known in the art to allow compression of the part of the needle tip shielding device 100 which is contacting an inner surface of the catheter unit, such as the inner surface of the catheter hub 200. When this part is not compressed, its effective outer diameter is slightly larger than the inner diameter of e.g. the catheter hub 200. When this part is compressed, the effective diameter is equal to or slightly smaller than the inner diameter of e.g. the catheter hub 200. Thus, when mounted in e.g. the catheter hub annular space, the needle tip shielding device will be detachably held therein by a normal force in combination with the inherent friction. The part is preferably made of a non-fragile polymer with an inherent strive to reach the uncompressed dimensions.

In the fully retracted position, the hollow needle 303 engages with the needle tip shielding device 100 by a stop member, i.e. engagement means, so that further backwards movement relative the needle tip shielding device 100 is prevented. The needle tip 304 may thus not be withdrawn past the proximal end of the needle tip shielding device 100. In addition, the needle tip 304 is protected by means for protecting the needle tip 304 in this position as described above herein. Thus, in the fully retracted position, the engagement means are synchronizing the movement of the needle tip shielding device 100 with the movement of the hollow needle 303 in the direction from the distal end towards the proximal end of the hollow needle 303, whereby a backwards movement of the hollow needle 303 in the direction from the distal end towards the proximal end of the hollow needle 303 results in essentially the same backwards movement of the needle tip shielding device 100. Engagement means, i.e. the stop member, constitute preferably an expansion region 305 on the shaft of the hollow needle 303 near the needle tip 304 which engages with a part, such as the hole 102, of the needle tip shielding device 100. Other engagement means include attachment by friction. The inner surface of the hole 102 and the outer surface of the hollow needle 303 near the needle tip 304 may then be provided with a certain roughness, i.e. friction elements 400, as known in the art, for secure engagement. Additional engagement means include a foldable string or strip 402 of defined unfolded length fastened at one end to the needle tip shielding device 100, and at the other end to the needle unit 300, as known in the art. As the fully retracted position is reached, the string or strip 402 is extended to its maximal length, whereby further withdrawal of the hollow needle 303 relative the needle tip shielding device 100 is prevented. Preferably, the length of the foldable string or strip 402 is less than the length of the needle 303.

After withdrawal of the hollow needle 303 to the fully retracted position, the needle tip shielding device 100 is disconnected from the catheter unit to allow disposal of the needle unit 300, in which the comprised needle tip 304 is protected from accidental contact. Such withdrawal is preferably achieved with a slight jerk backwards of the needle unit 300. Above described means for detachably attaching the needle tip shielding device 100 inside the catheter hub 200 are preferably adapted, as known in the art, to allow facile disconnection of the needle tip shielding device 100 without compromising the intended function of above described engagement means for engaging the hollow needle 303 with the needle tip shielding device 100.

It was surprisingly discovered that polished flat surfaces made of the same polymeric materials attract each other to a greater extent than the corresponding flat surfaces made of different polymeric materials. Without being bound to theory, we speculate that this difference in the attraction effect between same polymeric materials and different polymeric materials is due to reduced van der Waals attraction between different polymeric materials, as compared to same polymeric materials. In addition, without being bound to theory, we speculate that the tendency for formation of covalent bonds across two contacting surfaces of different polymeric materials is reduced in comparison to the case with same polymeric materials. In turn, traces of residing monomers or reactive functional groups may be contributing factors.

Thus, by having contacting parts of the catheter instrument (1000) made of different materials, in particular such parts that need to be separated from each other for achieving the desired functionality, the risk for malfunction due to the attraction effect is reduced. In particular, the contacting parts of the needle tip shielding device 100 are hence preferably made of a material different from the material of the corresponding contacting parts of the catheter unit, such as the catheter hub 200. Preferably, the needle tip shielding device 100 is made of a first polymeric material, and the catheter hub 200 is made of a second polymeric material.

According to one embodiment, the means of the needle tip shielding device 100 for protecting the needle tip 304 comprise one resilient arm 103.

According to one embodiment, the means of the needle tip shielding device 100 for protecting the needle tip 304 comprise a plurality of resilient arms, as known in the art.

According to one embodiment the needle tip shielding device 100 is positioned in the catheter hub annular space in the ready position.

According to one embodiment the needle tip shielding device 100 is positioned outside the catheter hub annular space in the ready position.

Referring to FIG. 1, there is provided a catheter instrument 1000 comprising a needle tip shielding device 100 according to an embodiment of the invention, a catheter hub 200 and a needle unit 300. The needle unit 300 is provided with connecting means 301 for connection to the catheter hub 200, and with connecting means 302 for connection to an external device, for example a syringe or the like. It is mechanically and hermetically fixed as known in the art, such as molded or glued, around the rear end of a hollow needle 303, whereby liquid passage is allowed in both directions, from the rear end of the needle unit 300 to and through a needle tip 304 of the hollow needle 303. The hollow needle 303 may be made of metal and of a type commonly used and well known in the medical art to penetrate the skin of a patient.

The needle tip shielding device 100 is fitted inside the catheter hub 200 so that the outer surface of the former is contacting the inner surface of the latter. Movement of the needle tip shielding device 100, relative the catheter hub 200, may be restricted by means of at least one protuberance 101, located on the outer surface 108 of the needle tip shielding device 100. Protuberance 101 is making a corresponding imprint in, and where it contacts, the inner surface of the catheter hub 200. The hollow needle 303 is longitudinally movable through a hole 102 in the needle tip shielding device 100. The hole 102 has a diameter adapted for the hollow needle 303 to be able to slide therein. The diameter of the hole 102 may, for example, be slightly larger that the outer diameter of the hollow needle 303, or the same. The hollow needle 303 is provided with an expansion region 305 near the needle tip 304. The expansion region 305 is a region on the hollow needle 303 where the effective diameter is larger than elsewhere on the needle in the direction towards the rear hollow needle 303. An increase in the effective diameter of the hollow needle 303 by expansion region 305 has the effect that this region is not movable through the hole 102.

The needle tip shielding device 100 is provided with a resilient arm 103, which is held out of its three dimensional equilibrium state, i.e. its normal resting position or resting state, by the outer surface of the hollow needle 303. The hollow needle 303 is, despite its contact with the resilient arm 103, longitudinally movable as it is arranged to slide on the same. The catheter hub 200 is connected to a catheter 201, which extends longitudinally in the same direction as the hollow needle 303. The catheter 201 is preferable flexible and of a type commonly used and well known in the medical art. The inner diameter of the catheter 201 may be slightly larger than the outer diameter of the hollow needle 303 and arranged so that the latter, as well as expansion region 305, may slide inside the former.

In the ready mode, i.e. before its use for the introduction of a catheter tube, the following characteristics of catheter instrument 1000 are valid: (i) Needle unit 300 is connected by connecting means 301 to the catheter hub 200. (ii) The hollow needle 303 is extending through the hole 102 of the needle tip shielding device 100, which is fitted inside the catheter hub 200, whereby movement of the needle tip shielding device 100 relative the catheter hub 200 is restricted. The hollow needle 303 is contacting the resilient arm 103 whereby this is forced out of its normal resting position. (iii) The hollow needle 303 is further extending through catheter 201 so that the needle tip 304 is protruding slightly past the opening of the catheter 201 in order to facilitate penetration of the skin of a patient.

When in ready mode, the catheter instrument 1000 may be used by a user, such as a nurse or other medical personnel, for the introduction of a catheter tube, such as catheter 201, in accordance with the following sequential steps: (i) Penetration of the skin of a patient by means of needle tip 304, followed by insertion of the catheter 201 so that its opening is located in the desired body cavity, such as the inside of a vein. (ii) Fastening of the catheter hub 200 on the skin of the patient by means well known in the art, such as with medical tape or the like. (iii) Disconnection of connecting means 301, followed by withdrawal of the hollow needle 303 by holding onto and pulling the needle unit 300 backwards until the needle tip shielding device 100 is disconnected, whereby the resilient arm 103 of the needle tip shielding device 100 is protecting the needle tip 304 so that it cannot penetrate skin by accident.

Figure 2:
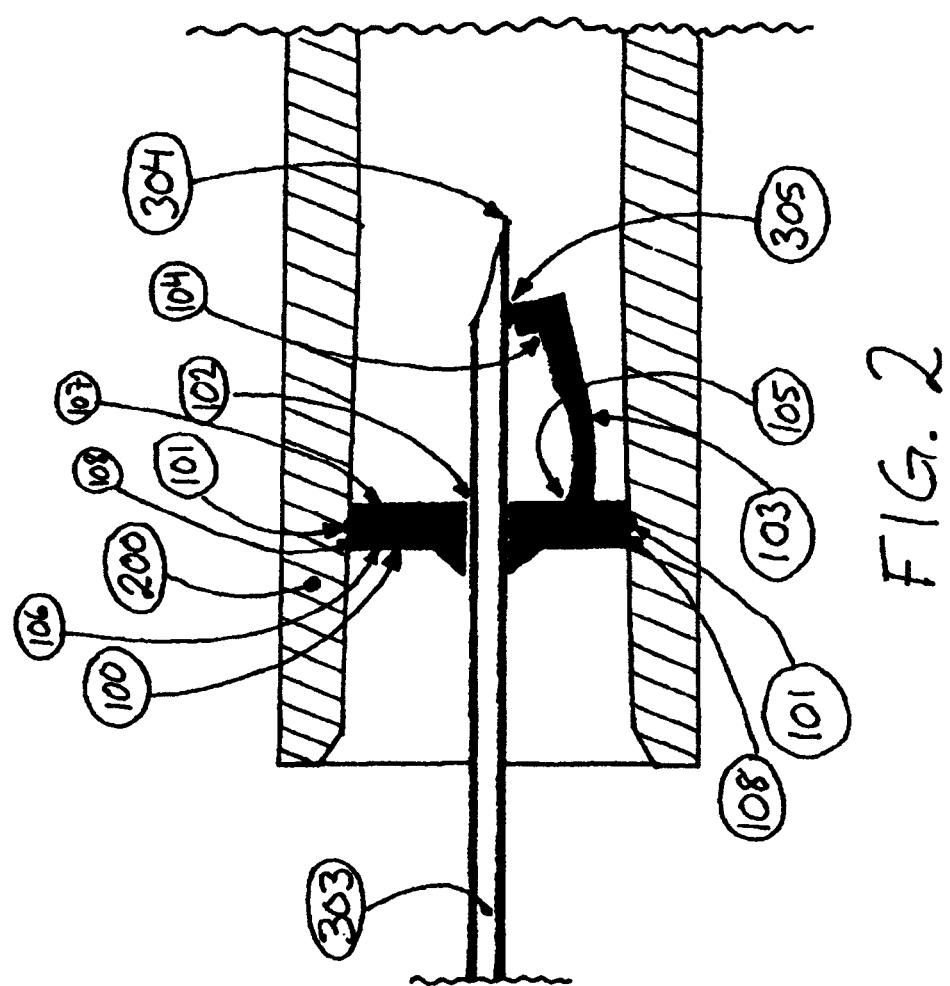
FIG. 2 is a cross section view from the side of the needle tip shielding device 100 of FIG. 1 fitted inside a catheter hub 200 with a hollow needle 303 withdrawn to the point where an expansion region 305 reaches a contact point of a resilient arm 103.
Figure 3:
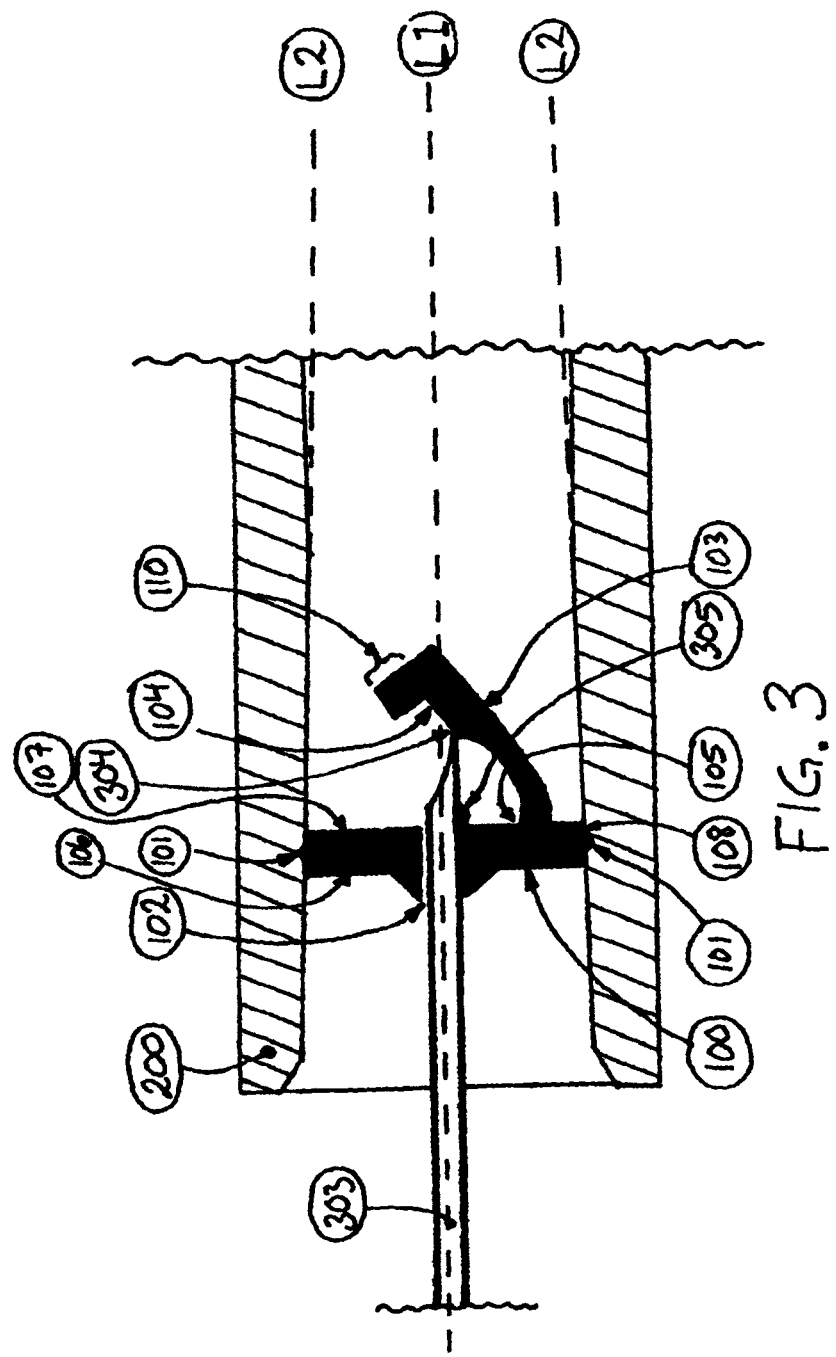
FIG. 3 is a cross section view from the side of the needle tip shielding device 100 of FIG. 1 fitted inside a catheter hub 200 with a hollow needle 303 withdrawn to the point where an expansion region 305 reaches a hole 102, whereby further backwards movement of the hollow needle 303 relative the catheter hub 200 is prevented without disconnection of the needle tip shielding device 100 from the catheter hub 200.
Figure 4:
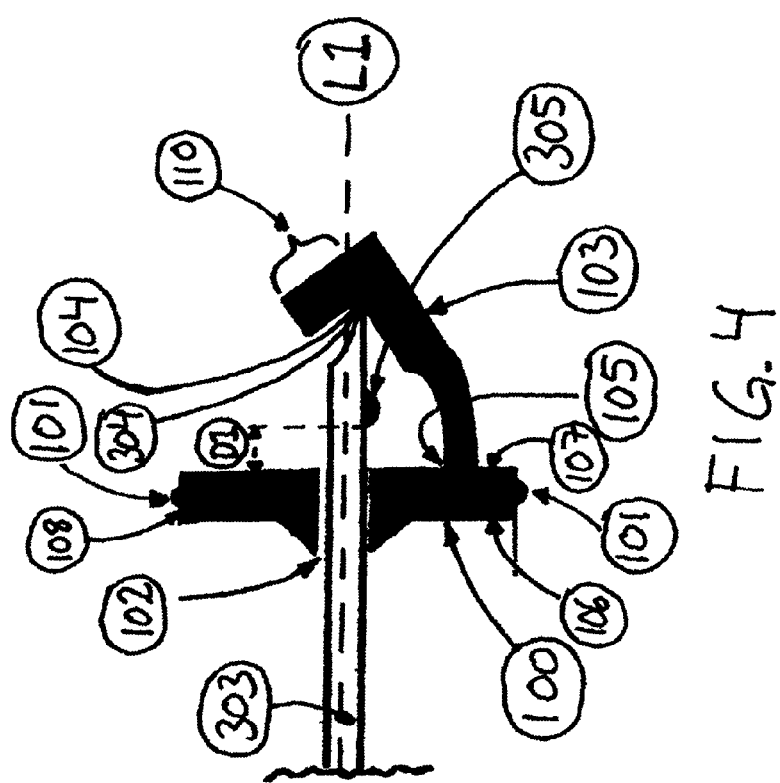
FIG. 4 is a cross section view from the side of the needle tip shielding device 100 of FIG. 1 disconnected from the catheter hub 200, with a hollow needle 303 pushed forward with the rear end of an expansion region 305 a distance Dl from the most forward edge of a hole 102, whereby a needle tip 304 coincidences with a corner 104.

With reference to FIGS. 2, 3 and 4, below follows a detailed description of the various events that occur upon withdrawal of the hollow needle 303 according to (iii) above:

When the hollow needle 303 has been withdrawn to the point where expansion region 305 reaches the contact point of the resilient arm 103, the latter may bend away slightly to allow easy passage of the former upon a slight increase in the force of withdrawal (FIG. 2). If the expansion region 305 is of a particular type and located on the hollow needle 303 such that the resilient arm does not come in contact with any area with increased effective diameter, the resilient arm does not have to bend away slightly. Examples of such an expansion region 305 include a protruding bump, e.g. a butt weld, which is facing away from the contact point of the resilient arm 103 on the hollow needle 303. Examples of other possible expansion regions 305 include a crimp or any other protruding distortion as well known in the art.

Further withdrawal of the hollow needle 303, to the point where the needle tip 304 passes the contact point of the resilient arm 103, results in that the latter strives toward its normal resting position, which is such that a part of the resilient arm 103, or an extension thereof, is in front of the needle tip 304 (FIG. 3). The resting position of the resilient arm 103 is such that the needle tip 304 will always project, in the longitudinal direction of the hollow needle 303, onto a point of the surface of the resilient arm 103 which is positioned between a corner 104 and the attachment point 105 of the resilient arm 103 independent of the degree of rotation of the hollow needle 303 around its longitudinal axis. The needle tip 103 is thus clamped and protected by the resilient arm 103.

When drawn backwards beyond this point, the hollow needle 303 may not be pushed in the forward direction again without being hindered by the resilient arm 103, or an extension thereof. Hence, if a user tries to push the hollow needle 303 forwards, the needle tip 304 may penetrate slightly into the resilient arm 103. Preferably the resilient arm 103 is arranged so that this penetration occurs in the corner 104 (FIG. 4).

Even further withdrawal of the hollow needle 303, to the point where the expansion region 305 reaches the hole 102, results in that the hollow needle 303 engages with, i.e. gets stuck in, in the needle tip shielding device 100 (FIG. 3). Additional increase in the force of withdrawal of the hollow needle 303 results in that the needle tip shielding device 100 disconnects from the catheter hub 200. The hollow needle 303 is thereby released from the catheter hub 200 together with the needle tip shielding device 100, which is effectively clamping the needle tip 304 and protecting a user from accidental contact with the same. The force needed to disconnect the needle tip shielding device 100 from the catheter hub 200 is, amongst other factors, depending on the angle between an imaginary line L1, which is equivalent with the extension of the hollow needle 303 and the center of the hole 102, and an imaginary line L2, which is a straight line extending in the same plane as L1 that coincides with two points on the surface of the needle tip shielding device 100 being in contact with the inner surface of the catheter hub 200, said points being located outside the surface of the protuberance 101 (FIG. 3). Preferably this angle is such that the needle tip shielding device 100 is not disconnected from the catheter hub when the hollow needle 303 is withdrawn until the expansion region 305 reaches the hole 102. The needle tip shielding device 100 is, however, preferably easily disconnected when the expansion region 305 reaches the hole 102, such as with, for example, a gentle jerk backwards. When the hollow needle 303 and the needle tip shielding device 100 have been released from the catheter hub 200, or when the needle tip shielding device 100 is fitted inside the catheter hub 200 and the needle tip 304 is clamped by the resilient arm 103, or an extension thereof, the hollow needle 303 might be pushed forward so that the rear end of the expansion region 305 is moved forward a distance D1 from the most forward edge of the hole 102, during which the needle tip 304 may slide on the surface of the resilient arm 103 until it coincides with the corner 104 (FIG. 4). Preferably, the location of the expansion region 305 on the hollow needle 303 is selected such that the distance D1 is minimized while still allowing the resilient arm 103, or an extension thereof, to clamp the needle tip 304 when the hollow needle 303 is withdrawn.

Connecting means 301 and 302 may independently be selected from various connection types allowing a user to connect and disconnect the needle unit 300 from the catheter hub 200, and the needle unit 300 from the external device, respectively, as desired. Examples of such connection types include Luer-Lok®, Luer-Slip®, and various types of bayonet sockets or the like, as well known in the art. Preferably, connecting means 301 and 302, in particular connecting means 302, are air tight so that no gas or liquid, such as blood or any other body liquid, may pass.

With reference to FIG. 4, according to one embodiment, the location of the expansion region 305 on the hollow needle 303 is selected such that the distance Dl is minimized while still allowing the resilient arm 103, or an extension thereof, to clamp the needle tip 304 when the hollow needle 303 is withdrawn.

According to one embodiment, the catheter hub 200 may be provided with additional devices and the like to facilitate its placement and optimize its use, as well known in the art. For example, it may be provided with valves, gaskets, fastening devices, means for drying blood residues of the needle, and the like.

The Needle Tip Shielding Device 100

Figure 5:
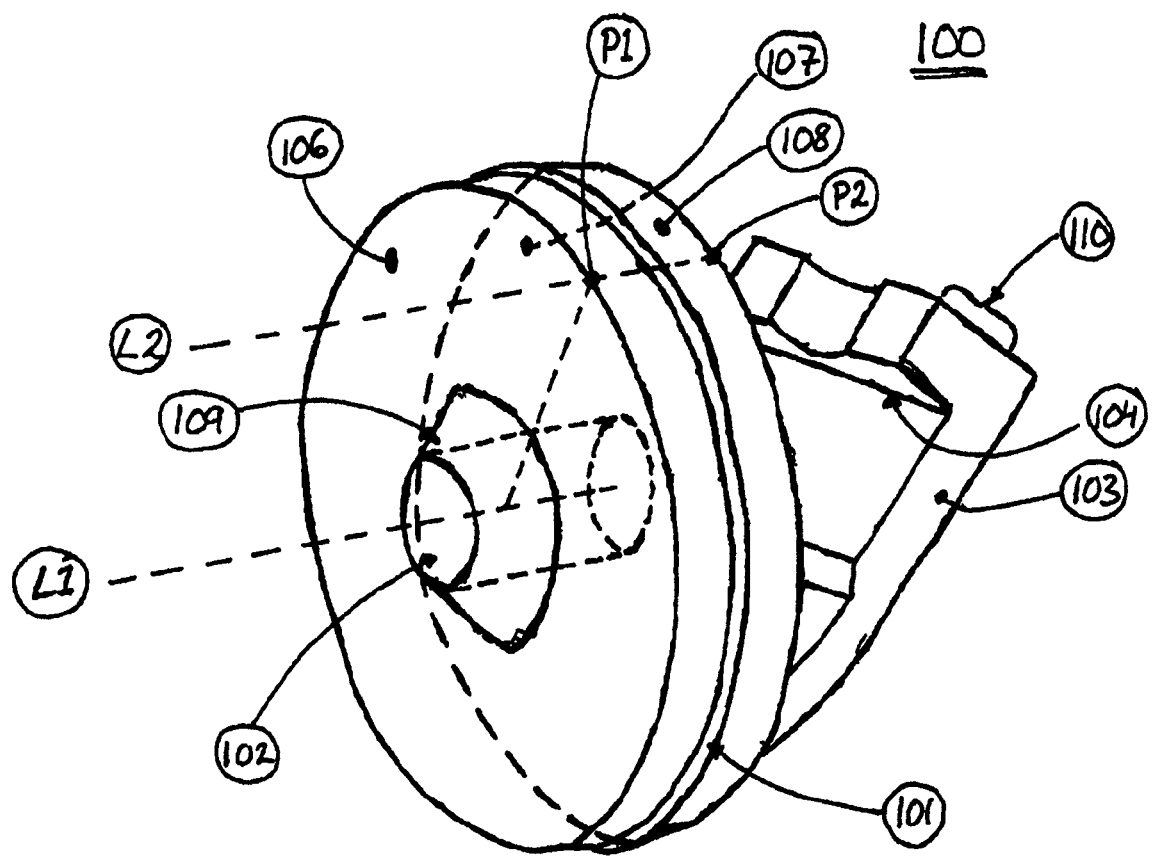
FIG. 5 is a perspective view of a needle tip shielding device 100 comprising a body with a circular rear side 106, a circular front side 107, an outer surface 108 connecting the circular rear side 106 and the circular front side 107, the circular hole 102 extending from the circular rear side 106 to the circular front side 107, and a resilient arm 103 extending from the front side 107 of the body, according to an embodiment of the invention.

With reference to FIG. 5, according to one embodiment of the invention, the needle tip shielding device 100 comprises a body with a rear side 106, a front side 107, an outer surface 108 connecting the rear side 106 and the front side 107, a hole 102, preferably being circular, extending from the rear side 106 to the front side 107, and a resilient arm 103 extending from the front side 107 of the body. The rear side 106 and the front side 107 may be essentially flat and may be essentially parallel to each other. The hole 102 may extend essentially perpendicular to the plane of the rear side 106, and to the plane of the front side 107. The hole 102 is preferably positioned essentially at the center of the rear side 106, and at the center of the front side 107. The straight imaginary line L2 is coinciding with a point P1 at the edge between the rear side 106 and the outer surface 108, and with a point P2 at the shortest possible distance from point P1 at the edge between the front side 107 and the outer surface 108. At any pair of points P1 and P2, the part of line L2 extending from P1 to P2 preferably essentially coincides with the outer surface 108. The straight imaginary line L1 extending longitudinally through the center of the hole 102 is preferably essentially coinciding with the plane of any line L2. Any imaginary straight line, which is parallel with L1 and extending longitudinally through the hole 102, coincides with a point at the surface in between the attachment point 105 (not shown in FIG. 5) and the corner 104 of the resilient arm 103, when the resilient arm is in its resting state. The attachment point 105 is the edge which defines the transition between the front side 107 and the side of the resilient arm 103 which is closest to the hole 102. The corner 104 defines a sudden bend of the resilient arm 103 towards the plane of the front side 107, when the resilient arm 103 is in its resting state. Thus, the resilient arm 103 attains an L-shaped form, where the horizontal line of the L corresponds to a back-hooking elongation 110 of the resilient arm 103. The shape of the needle tip shielding device 100 according to the present invention has, in comparison to devices of the prior art, the advantage that it will act as a shield at the moment it disconnects from the catheter hub 200. Thereby it provides excellent protection per se against drops of blood or body fluid that may move outwards from the interior of the catheter hub 200 as the hollow needle 303 is removed.

Preferably, the resilient arm 103 is dimensioned, and attached at a position on the front side 107, such that it or the back-hooking elongation 110 may never contact the inner surface of the catheter hub 200 independent of the position of the hollow needle 303. Such a contact would potentially adventure the intended placement of the needle tip shielding device inside the catheter hub 200.

Preferably, the area of the back-hooking elongation 110 is fully covering the projecting area of the hole 102 when the needle tip 304 is clamped in the corner 104, i.e. protected, while the resilient arm 103 is maximally forced out of its resting state (as dependant on the rotation of the hollow needle 303 whereby the needle tip 304 attains different coordinates). This minimizes the risk of uncovering the needle tip 304 on the event that the resilient arm 103 gets bent by e.g. a sideways applied external force. Such a setup is not possible when more that one arm or jaw, corresponding to the resilient arm 103, is used in collaboration as they counteract each other in this regard.

According to one embodiment, the needle tip shielding device 100 has a circular shape, such that the rear side 106 and the front side 107 projects a circle from a view along the direction of the hollow needle 303.

According to one embodiment, the needle tip shielding device 100 has an elliptic shape, such that the rear side 106 and the front side 107 projects an ellipse from a view along the direction of the hollow needle 303.

According to one embodiment, the hole 102 is centered in the rear side 106 and in the front side 107.

According to one embodiment, the rear side 106 has a diameter in the range of 3 to 6 mm, preferably 3.9 to 4.3 mm, and even more preferred 4.1 to 4.15 mm.

According to one embodiment, the rear side 106 is provided with a cone-shaped elevation 109 through which the hole 102 is extending. The effective length of the hole 102 is thereby increased which, for example, allows a better guidance of the hollow needle 303 without having to increase the area of the outer surface 108 by increasing the distance between P1 and P2. Furthermore, the cone-shaped area might be provided with means known in the art, such as a circular scraper, which cleans off residues of e.g. blood from the hollow needle 303 as this is withdrawn.

According to one embodiment, the width of the outer surface 108 in the longitudinal direction, i.e. the distance between the front side 107 and the rear side 106, is between 0.5 to 15 mm, preferably 1 to 3 mm.

According to one embodiment, the diameter of the hole 102 is in the range from 0.2 to 1.5 mm, such as 0.62 to 0.64 mm.

Figure 6:
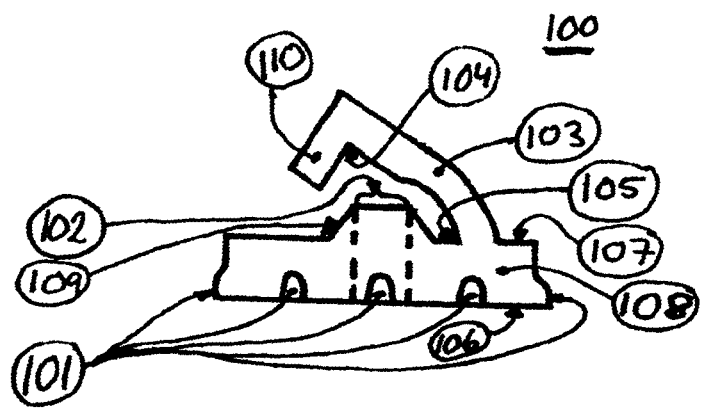
FIG. 6 is a view from the side of a needle tip shielding device 100 comprising a cone-shaped elevation 109 on the front side 107, with a plurality of protuberances 101 on the outer surface 108, according to an embodiment of the invention.

According to one embodiment, the front side 107 is provided with the cone-shaped elevation 109 (FIG. 6). The arrangement, e.g. positioning and dimensions, of the resilient arm 103 and the cone shaped elevation is such that the intended function of the resilient arm 103 is not adventured. Thus, the resting position of the resilient arm 103 is such that the needle tip 304 will always project, in the longitudinal direction of the hollow needle 303 (not shown) positioned in the hole 102, onto a point of the surface of the resilient arm 103 which is positioned between a corner 104 and the attachment point 105 of the resilient arm 103 independent of the degree of rotation of the hollow needle 303 around its longitudinal axis. When the cone-shaped elevation 109 is positioned on the front side 107, the rear side 106 is preferably essentially flat. This allows for facile assembly of the needle tip shielding device 100 in the catheter hub 200 by pressing it into the same by employment of a tool which is contact with essentially the entire surface of the rear side 106.

Figure 7:
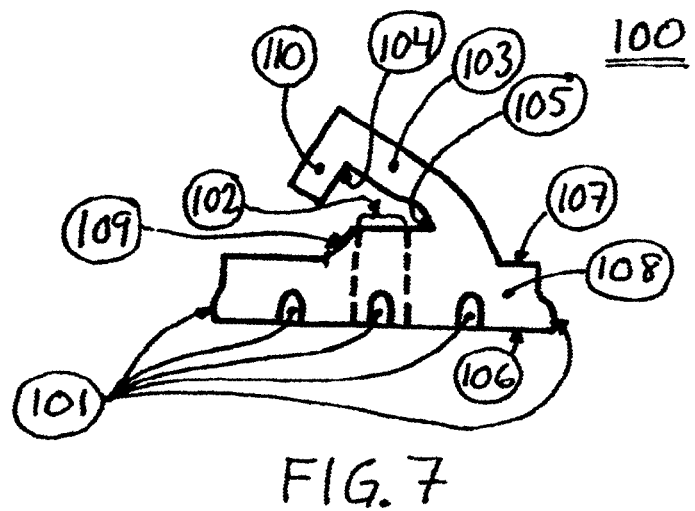
FIG. 7 is a view from the side of the needle tip shielding device 100 of FIG. 6, in which the cone shaped elevation 109 is merged with the resilient arm 107, according to an embodiment of the invention.

According to one embodiment, the cone shaped elevation 109 is merged with the resilient arm 107 (FIG. 7). The resilient arm 103 is thereby additionally forced into a protective resting position which decreases the risk of functional failure of the needle tip shielding device 100. In addition, the needle tip shielding device 100 may be manufactured more easily by e.g. molding.

According to one embodiment, the needle tip shielding device 100 is provided with the aforementioned protuberance 101 located on the outer surface 108. The protuberance 101 will make an imprint in the surrounding material of the catheter hub 200 when the needle tip shielding device 100 is positioned therein. The mechanical interaction between the protuberance 101 and the catheter hub 200, and the corresponding imprint caused by the former, will reduce the risks of unintentional disconnection of the needle tip shielding device 100 from the catheter hub 200.

According to one embodiment, the protuberance 101 is an annular protuberance extending in a continuous loop around the outer surface 108.

According to one embodiment, the protuberance 101 is an annular protuberance extending in a continuous loop around the outer surface 108, and being located in a plane perpendicular to L1.

According to another embodiment, the protuberance 101 may be a singularity or a plurality of protuberances independently selected from the group consisting of dots, straight elongated shapes, curved elongated shapes, V-shapes, and any other shape known in the art to make an imprint in an object in order to prevent relative movement versus this, such as the shapes on the surface of a tire optimized for use on soft ground.

According to one embodiment, the protuberance 101 may be made of a material with a hardness which is greater that the hardness of the inner surface of the catheter hub 200, in order to effectively accomplish an imprint in the latter. Preferably, the protuberance 101 is made of the same material as the rest of the needle tip shielding device 100, in order to allow for a facile and economically advantageous production of the same.

According to one embodiment, the type, multiplicity and dimension of protuberance 101 is selected such that no unintentional disconnection of the needle tip shielding device 100 from the catheter hub 200 may occur, yet allowing facile intentional disconnection when the hollow needle 303 is withdrawn. For example, the protuberance 101 may be an annular protuberance extending in a continuous loop around the outer surface 108 with a height in the range of 0.01 to 0.3 mm, such as 0.03 to 0.1 mm, from the same.

Figure 8:
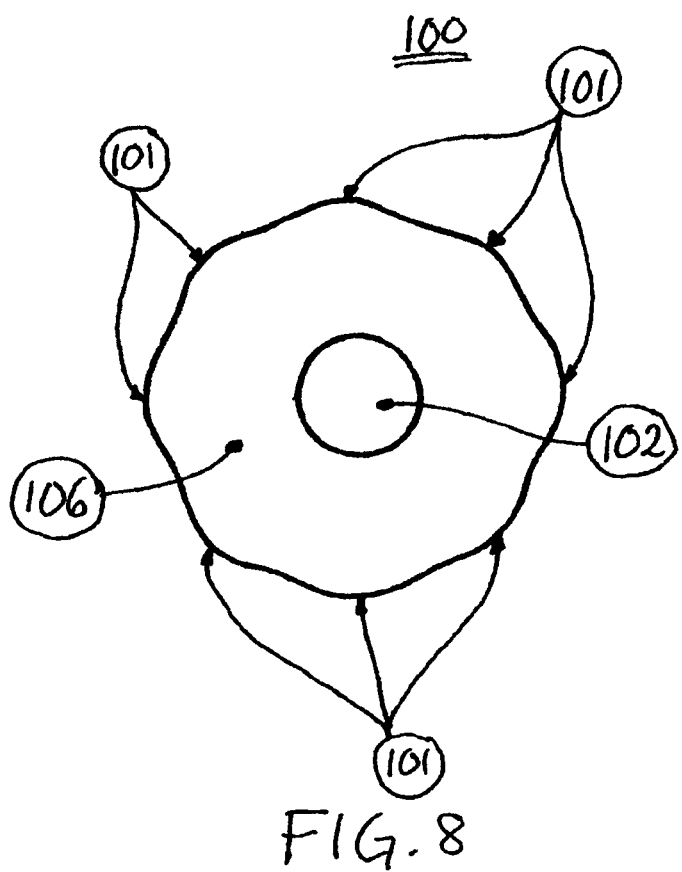
FIG. 8 is a view from the rear side 106 of the needle tip shielding device 100 of FIG. 6 or 7, according to an embodiment of the invention.

According to one embodiment, the protuberance 101 may be a plurality of protuberances on the outer surface 108 (FIGS. 6 to 8). These may begin at the corner between the rear side 106 and the outer surface 108 and extend in a plane perpendicular to the plane of the rear side 106 and/or the front side 107, toward the front side 107. Preferably, they are evenly spread along the extension of the outer surface 108. Their extension along the outer surface 108 may be 10 to 95% of the distance between the rear side 106 and the front side 107 along the outer surface 108. Preferably, the endings being closest to the front side 107 consists of a smooth slope to allow facile insertion in a catheter hub 200. The plurality of protuberances on the outer surface 108 may have a height in the range of 0.01 to 0.3 mm, preferably 0.03 to 0.1 mm, and more preferred 0.04 to 0.06 mm, from the same. The plurality of protuberances on the outer surface 108 may consist of 1 to 20 individual protuberances, preferably 2 to 12, which may be of the same or of different lengths and/or heights. Preferably, they are of equal length and height.

Figure 9:
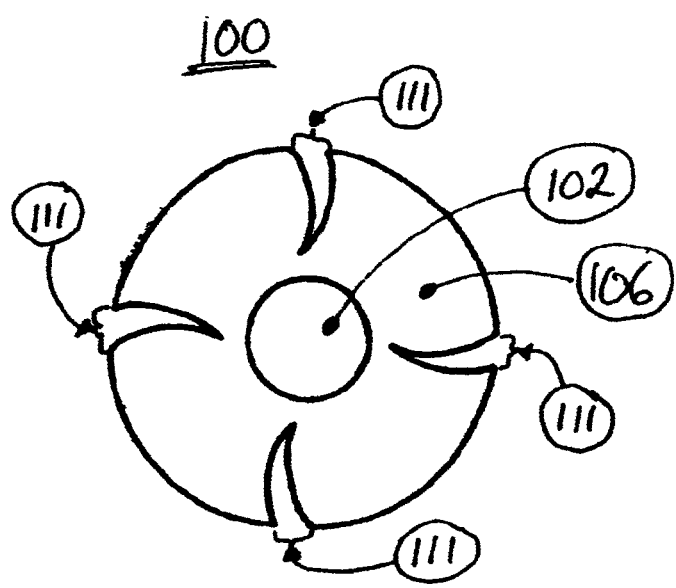
FIG. 9 is a view from the rear side 106 of a needle tip shielding device 100 comprising evenly dispersed curved slits 111 extending in longitudinal direction of the needle tip shielding device 100, according to an embodiment of the invention.
Figure 10:
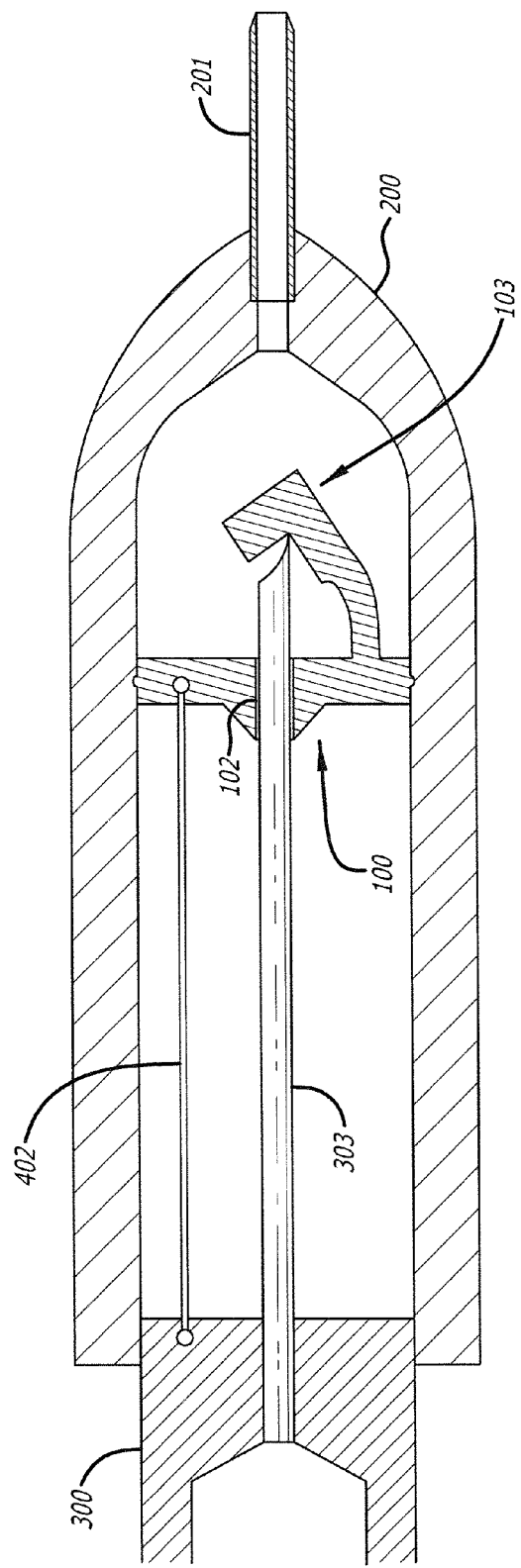
FIG. 10 is a cross section view from the side of the needle catheter instrument 1000, similar to FIG. 1, but depicting a different embodiment of a stop member.
Figure 11:
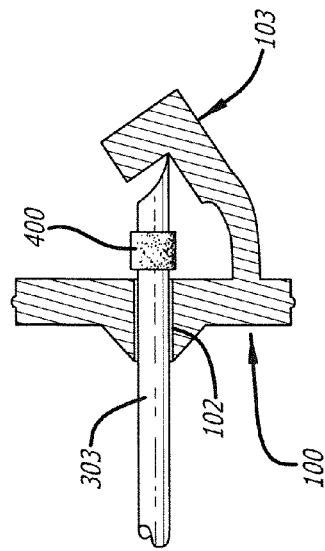
FIG. 11 is a cross section view from the side of the needle tip shielding device 100, similar to FIG. 4, but depicting a different embodiment of a stop member.

According to one embodiment, with reference to FIG. 9, the needle tip shielding device 100 is be provided with slits 111. These slits 111 may be 1 to 20, preferably 2 to 8, and are preferably evenly dispersed around the outer surface 108. They may extend essentially in the longitudinal direction of the needle tip shielding device 100 from the rear side 106 to the front side 107. Their extension from the outer surface 108 toward the center axis, i.e. line L1, may be essentially along the shortest distance from the outer surface 108 to the center axis, or along a line from one point at the outer surface 108 to another point at the outer surface 108 which does not cross the center axis. In the former case, the slits are 111 are preferably curved. In the latter case, the slits 111 may be curved or straight. Advantages of slits 111 as described above include the possible combination of a catheter hub 200 made of a first material, with a needle tip shielding device 100 of a second material, wherein the first material is harder than the second, since no imprints need to be made for achieving the desired function.

According to one embodiment, any part of the needle tip shielding device 100, such as the protuberance 101 or the outer surface 108, which may contact any other part of the catheter instrument 1000, such as the catheter hub 200, is made of a material which is different from the material of the part of the catheter instrument 1000 it may contact. Advantageously, the risk for malfunction of the catheter instrument 1000 due to the attraction effect is thus minimized.

According to one embodiment, the surface of outer surface 108, the protuberance 101, and the contacting surface of the inside of the catheter hub 200 is polished to minimize friction between these surfaces, as known in the art. The outer surface 108 and the protuberance 101 is made of a material, preferably polymeric or plastic, which is different from the material, preferably polymeric or plastic, of the inside of the catheter hub 200. The potential additional factors, such as friction and the attraction effect, which may affect the degree of force needed to release the needle tip shielding device 100 from the catheter hub 200, are thereby reduced. Thus, the force needed to release the needle tip shielding device 100 from the catheter hub 200 then becomes mainly dependant on the design and dimensions of the protuberance 101. The reduction of these additional factors allow for production and assembly of a catheter instrument 1000 with decreased variation in the force needed to eject the needle tip shielding device 100, which increases e.g. safety.

According to one embodiment, the inclination of the outer surface 108 of the needle tip shielding device 100, i.e. the angle between lines L1 and L2, is within in the range from 0° to 10°, preferably in the range from 4° to 8°, and even more preferred 6°. Preferably, the inclination of the outer surface 108 is essentially the same as the inclination of the catheter hub 200 where the needle tip shielding device 100 is mounted when the catheter instrument 1000 is in the ready mode. This maximizes the contact surface between the outer surface 108 and the inside of the catheter hub 200, whereby accidental detachment of the needle tip shielding device 100 from the catheter hub 200 is hindered.

According to one embodiment, the inclination of the outer surface 108 of the needle tip shielding device 100, i.e. the angle between lines L1 and L2, is the same as the angle used in well known or standardized detachable conical fittings, such as fittings used for syringes, e.g. the Luer taper. Advantageously, the needle tip shielding device 100 thus becomes highly generally applicable for assembly in e.g. readily available standard catheter hubs.

According to one embodiment, the needle tip shielding device 100 is made of a plastic or polymeric material. Preferably, the plastic or polymeric material has a suitable combination, for its intended purpose, of tenacity, rigidity, fatigue resistance, elasticity, and creep deformation resistance. The selection of a suitable plastic or polymeric material may easily be made by the one skilled in the art. The one skilled in the art may also perform standard experiments in order to screen a range of plastic or polymeric materials, whereby a suitable plastic or polymeric material may be selected on the basis of the results of such experiments. A suitable plastic or polymeric material has a high creep deformation resistance, i.e. it has a low tendency to slowly move or deform permanently under the influence of an applied external pressure. Hence, a catheter instrument, such as the catheter instrument 1000 of the present invention, comprising a needle tip shielding device 100 with protuberance 101, may be stored in the assembled ready mode for a prolonged time without extensive creep deformation of protuberance 101, which would otherwise make the needle tip shielding device 100 more prone to involuntary disconnection from the catheter hub 200. A suitable plastic or polymeric material has, furthermore, a suitable elasticity and high three-dimensional memory to allow for the resilient arm 103 to retain its resting state and clamp the needle tip 304 even after prolonged storage, during which the resilient arm 103 has been forced out of this state. In addition, the tenacity of the plastic or polymeric material is preferably such that the needle tip 304 may penetrate slightly into, but not through the same.

An advantage of the use of a plastic or polymeric material for the construction of the needle tip shielding device 100, in comparison to e.g. metal, is the greater freedom of variation of various details of the same. For example, a plastic needle tip shielding device 100 according to the invention may be more conveniently molded than the corresponding metallic article. Another advantage includes the possibility to colour-code a plastic needle tip shielding device 100 according to the invention, for example according to the needle size. Yet another advantage of a plastic or polymeric needle tip shielding device 100 according to the invention is the fact that the needle tip 304 may penetrate slightly into the corner 104 of the resilient arm 103. This represents an "active" and safer shielding principle, in comparison to "passive" shielding of the prior art, whereby the resilient arm 103 is even further locked onto the needle tip 304 and hence additionally restricted from movement out of the safe position. Yet another advantage of a plastic or polymeric needle tip shielding device 100 according to the invention is the fact that a metallic needle sliding through the hole 102, and on the resilient arm 103, does not give rise to a scraping vibration and sound of the uncomfortable type related to a metal needle sliding on and/or through a metal clip. Yet another advantage of a plastic or polymeric needle tip shielding device 100 according to the invention is the higher chemical inertness and/or resistance, in comparison to metal, towards e.g. corrosion and reaction with chemicals that might leak from the plastic surrounding constituted by a catheter hub and comprising silicon gaskets and the like. Yet another advantage of a needle tip shielding device 100, like a plastic or polymeric needle tip shielding device 100, according to the invention, is that it may be molded and produced in one functional piece, i.e. it does not have to be assembled by the combination of more than one separate article like other corresponding devices of the prior art. Hence, a reduction in the cost of production is resulting. Yet another advantage of a plastic or polymeric needle tip shielding device 100 according to the invention is the highly reduced tendency, in comparison to metal or other corresponding devices with sharp edges, of release of e.g. microscopic plastic chips by the scraping of the plastic catheter hub when the needle tip shielding device 100, or a corresponding device, is ejected from the former upon withdrawal of the needle. Accordingly, the tendency for formation of scrape marks, which may result in leakage through the affected connector, is greatly reduced.

According to one embodiment, the needle tip shielding device 100 is made of a thermoplastic polymer.

According to one embodiment, the needle tip shielding device 100 is made of a thermoplastic polymer comprising crystalline and amorphous alternating regions.

According to one embodiment, the needle tip shielding device 100 is made of a plastic or polymeric material selected from the group consisting of POM, PBTP, LCP, PA, PSU, PEI, PC, and PPO/SB.

According to one embodiment, the needle tip shielding device 100 is made of a thermoplastic elastomer selected from the group consisting of a styrenic block copolymer, a polyolefinic mixture, an elastomeric alloy, a thermoplastic polyurethane, a thermoplastic copolyester, and a thermoplastic polyamide.

According to one embodiment, the needle tip shielding device 100 is made of a plastic or polymeric material selected from the group consisting of Styroflex®, Kraton®, Pellethane®, Pebax®, Arnitel®, Hytrel®, Dryflex®, Santoprene®, Geolast®, Sarlink®, Forprene®, Alcryn®, and Evoprene®.

According to one embodiment, the needle tip shielding device 100 is made of a plastic or polymeric material selected from the group consisting of medical grade liquid crystal polymer, for example Vectra® LCP, polyethylene, and ultra high molecular weight polyethylene.

According to one embodiment, the needle tip shielding device 100 is made of polysulfon or polyoxymetylen.

According to one embodiment, the needle tip shielding device 100 is provided with at least one protuberance 101, a resilient arm 103, and made of a plastic or polymeric material with a suitable combination of tenacity, rigidity, fatigue resistance, elasticity, and creep deformation resistance, for assembly in a catheter hub 200. For example, the plastic or polymeric material may be polyoxymethylene (POM), polybutylen terephthalate (PBTP) or polysulfone (PSU), or any other material as known in the art with similar suitable properties. Preferably the plastic or polymeric material is different from the material of the catheter hub 200 in order to minimize the attraction effect. A majority of standard catheter hubs 200 are made of at least one polymer produced from substituted or unsubstituted ethene by a polymerization reaction in which the double bond of said ethane is converted to a single bond, for example polypropylene, polyethylene, or propylene/ethylene co-polymers. Thus, POM, PBTP or PSU, or any other material as known in the art with similar suitable properties which is not the same as the material of the catheter hub 200, may advantageously be used as the material of a generally applicable needle tip shielding device 100.

According to one embodiment, the needle tip shielding device 100 is made of a thermoplastic polymer comprising covalently bond O or S atoms. Preferably the thermoplastic polymer is different from the material of the catheter hub 200 in order to minimize the attraction effect. A majority of standard catheter hubs 200 are made of polymers that do not comprise covalently bond O or S atoms. Thus, thermoplastic polymer comprising covalently bond O or S atoms may advantageously be used as the material of a generally applicable needle tip shielding device 100.

According to one embodiment, the angle inside the corner 104 is within the range from 60° to 110°, preferably 80° to 100°, more preferred 85° to 95°, and most preferred 90°.

According to one embodiment, the length of the back-hooking elongation 110, measured in its elongation from the corner 104 to the most protruding part, is at least 0.5 times the diameter of the hole 102, such as 0.5 to 6 times the diameter of the hole 102. It is preferably dimensioned such that no part of the resilient arm 103 is brought in contact with the inner surface of the catheter hub 200 at any location of the hollow needle 303 when the needle tip shielding device 100 is mounted in the catheter hub 200.

According to one embodiment, the back-hooking elongation 110 may comprise a groove with a partial circular shape, as well known in the art, provided and dimensioned to guide and allow the hollow needle 303 to slide thereon when withdrawn.

According to one embodiment, the resilient arm 103 may be dimensioned such that its most protruding part when being forced out of its resting position by the hollow needle 303 is in the range of 0.3 to 3 times the diameter of the front side 107, as measured from the attachment point 105.

According to one embodiment, the width and placement of the resilient arm 103 is such that no part of the resilient arm 103, or the back-hooking elongation 110, is brought in contact with the inner surface of the catheter hub 200 at any location of the hollow needle 303.

According to one embodiment, the width of the resilient arm 103 is in the range of 0.2 to 0.9 times the diameter of the front side 107 and selected such that it can not be bent aside to expose the needle tip 304 under normal circumstances.

According to one embodiment, the thickness and the material of the resilient arm 103 are selected such that the hollow needle 303 may never penetrate through the resilient arm 103 by a user under normal circumstances.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:
1. A catheter instrument comprising:
a needle comprising a hollow needle shaft and a needle tip;
a needle carrying unit configured to hold the needle therein;
a catheter unit having a proximal end and a distal end defining an axis therebetween, the catheter unit comprising: a catheter hub, the catheter hub having an interface surface, and a catheter, the needle carrying unit adapted to be removably mounted within a proximal end of the catheter hub, with the needle slidable along the axis, to be projected in a distal direction and retracted in a proximal direction;
a needle tip shielding device having a round body adapted to be removably mounted within the catheter hub, the needle tip shielding device including:
a front surface,
a rear surface,
an elevation on at least one of the front and rear surfaces and including a hole positionable along the axis and configured to allow passage of the needle therethrough,
at least one interface surface configured to be removably attached to the interface surface on the catheter hub, and
a self-biased resilient needle tip shielding arm, the needle tip shielding arm including a first arm portion projecting from the front surface of the round body in a direction along the axis,
the first arm having a proximal end attached to the front surface and a distal end, and a second arm portion extending from the distal end of the first arm portion in a direction transverse to the first arm portion, at least a portion of the needle tip shielding arm being made of a first polymeric material; and
a stop member on the needle shaft and configured to prevent the needle tip shielding device from distal movement relative to the needle when the needle is retracted in the proximal direction;
wherein when the needle is projected into the catheter in the distal direction, the self-biased resilient needle tip shielding arm is pushed in a first direction away from the axis by the needle; and
wherein when the needle is retracted in the proximal direction, the self-biased resilient needle tip shielding arm, under the force of its own self-bias and resiliency, moves in the proximal direction, the at least a portion of the needle tip shielding arm made of the first polymeric material shielding the needle tip from subsequent projection in the distal direction,
wherein the interface surface of the needle tip shielding device is made at least partly of the first polymeric material and the interface surface of the catheter hub is made at least partly of a second polymeric material, the second polymeric material being different from the first polymeric material; and wherein when the needle is fully retracted in the proximal direction to a fully retracted position, the first polymeric material of the interface surface of the needle tip shielding device, and the second polymeric material of the interface surface of the catheter hub, are configured to facilitate removal of at least the needle tip shielding device from the catheter hub.

2. A catheter instrument according to claim 1, wherein the needle tip shielding device is positioned in a catheter hub annular space in a ready position.

3. A catheter instrument according to claim 1, wherein at least one of the needle tip shielding device and the catheter hub comprises a protuberance for detachably engaging and forming an imprint in the other of the at least one of the needle tip shielding device and the catheter hub.

4. A catheter instrument according to claim 1, wherein the stop member comprises an expansion region on the needle near the needle tip for engagement with the needle tip shielding device or the needle carrying unit, thereby preventing distal movement of the needle tip shielding device relative to the needle.

5. A catheter instrument according to claim 1, wherein the stop member comprises at least one of a friction element, a foldable string, and a stripe having a length less than a length of the needle.

6. A catheter instrument according to claim 1, wherein the self-biased resilient needle tip shielding arm defines a general L-shaped configuration.

7. A catheter instrument according to claim 1, wherein the needle tip shielding device further comprises: at least one protuberance.

8. A catheter instrument according to claim 1, wherein the needle tip shielding device further comprises: at least one slit.

9. A catheter instrument according to claim 1, wherein an outer surface of the needle tip shielding device is provided with a friction element comprising a rough surface.

10. A catheter instrument according to claim 1, wherein the second arm portion of the self-biased resilient needle tip shielding arm joins the first arm portion of the self-biased resilient needle tip shielding arm to define a corner, the corner being configured to receive at least a tip of the needle when the needle is in the fully retracted position.

11. A catheter instrument according to claim 1, wherein the facilitation of removal results from the different first and second polymeric materials.

12. A catheter instrument comprising:
a hollow needle comprising a needle shaft and a needle tip;
a needle carrying unit configured to support the needle;
a catheter unit having a proximal end and a distal end defining an axis therebetween, the catheter unit comprising a catheter hub, and a catheter, the needle carrying unit and the needle being removably mounted in the catheter hub and movable along the axis in a proximal direction and a distal direction;
a needle tip shielding device having a round body adapted to be removably mounted within the catheter hub, the needle tip shielding device including at least:
a front surface,
a rear surface,
an elevation on at least one of the front and rear surfaces and including an aperture positionable along the axis and configured to allow passage of the needle therethrough, and
a biased needle tip shielding arm including:
a first arm portion having a proximal end and a distal end, the proximal end attached to and projecting from the front surface of the round body in a direction along the axis, and
a second arm portion extending from the distal end of the first arm portion in a direction transverse to the first arm portion, at least a portion of the needle tip shielding arm being made of a first polymeric material; and
a stop member on the needle shaft,
wherein when the needle is in a ready position, with the needle projecting into the catheter, the needle is at least partly disposed in, and slidable within, the needle tip shielding device;
wherein when the needle is in a fully retracted position, in which said needle tip is prepared to be completely withdrawn from said catheter, said needle tip shielding arm made of the first polymeric material shields the needle tip from movement in the distal direction by moving across the axis;
wherein the stop member prevents the needle tip shielding device from distal movement relative to the needle in the fully retracted position;
wherein the needle tip shielding device contacts the catheter hub via at least one interface surface between the needle tip shielding device and the catheter hub, the at least one interface surface being defined by a first interface surface on the needle tip shielding device, and a second interface surface on the catheter hub;
wherein the first interface surface on the needle tip shielding device is made at least partly of the first polymeric material, and the second interface surface on the catheter hub is made at least partly of a second polymeric material, the first polymeric material being different from the second polymeric material; and
wherein when the needle is in the fully retracted position, the first polymeric material of the interface surface of the needle tip shielding device, and the second polymeric material of the interface surface of the catheter hub, are configured to facilitate removal of at least the needle tip shielding device from the catheter hub, the facilitation of removal resulting from the different first and second polymeric materials.

* * * * *